United States Patent [19]

Dantanarayana et al.

[11] Patent Number: 5,646,142

[45] Date of Patent: Jul. 8, 1997

[54] THIOPHENE SULFONAMIDES USEFUL AS CARBONIC ANHYDRASE INHIBITORS

[75] Inventors: Anura P. Dantanarayana, Fort Worth; Thomas R. Dean, Weatherford; Jesse A. May, Fort Worth, all of Tex.

[73] Assignee: Alcon Laboratories, Inc., Fort Worth, Tex.

[21] Appl. No.: 272,896

[22] Filed: Jul. 8, 1994

[51] Int. Cl.[6] .................... C07D 513/04; A61K 31/54
[52] U.S. Cl. ........................... 514/226.5; 544/48
[58] Field of Search ............... 514/226.5; 544/48

[56] References Cited

U.S. PATENT DOCUMENTS

| | | | |
|---|---|---|---|
| 4,619,939 | 10/1986 | Maren | 514/363 |
| 4,746,745 | 5/1988 | Maren | 548/139 |
| 4,797,413 | 1/1989 | Baldwin et al. | 514/432 |
| 5,153,192 | 10/1992 | Dean et al. | 514/226.5 |
| 5,240,923 | 8/1993 | Dean et al. | 514/226.5 |
| 5,308,863 | 5/1994 | Baldwin et al. | 514/431 |

FOREIGN PATENT DOCUMENTS 0 452 151 A1   4/1991   European Pat. Off. .

*Primary Examiner*—John M. Ford
*Attorney, Agent, or Firm*—Sally Yeager

[57] ABSTRACT

New thiophene sulfonamides useful as carbonic anhydrase inhibitors are disclosed. Methods for using the compounds to control IOP are also disclosed.

9 Claims, No Drawings

THIOPHENE SULFONAMIDES USEFUL AS CARBONIC ANHYDRASE INHIBITORS

FIELD OF THE INVENTION

The present invention relates to new thiophene sulfonamides useful in lowering and controlling intraocular pressure.

BACKGROUND OF THE INVENTION

Glaucoma is a disease of the eye which is characterized by a progressive loss of visual field due to irreversible damage to the optic nerve. If untreated, this condition can result in blindness. This loss of visual field, in one form of primary open angle glaucoma, that is, chronic primary open angle glaucoma, hereinafter POAG, is associated with a sustained increase in the intraocular pressure (IOP) of the diseased eye. In addition, elevated intraocular pressure without visual field loss, or ocular hypertension, can be indicative of the early stages of POAG.

There are a number of therapies that target reducing the elevated IOP associated with ocular hypertension or POAG. The most common feature the topical administration of a beta adrenergic antagonist (beta-blocker) or a muscarinic agonist. These treatments, while effective in lowering IOP, can also produce significant undesirable side effects.

Another less common treatment for ocular hypertension or POAG is the systemic administration of carbonic anhydrase inhibitors; however, this therapy can also bring about unwanted side effects, such as nausea, dyspepsia, fatigue, and metabolic acidosis. Topical administration of carbonic anhydrase inhibitors can be used to control IOP with a reduced risk of encountering the aforementioned systemic side effects. U.S. Pat. Nos. 5,153,192; 5,240,923; 4,797,413; 5,308,863; and EPO 91/452,151A1 disclose topically dosed sulfonamides which lower IOP by inhibiting carbonic anhydrase.

SUMMARY OF THE INVENTION

The present invention is directed to new thiophene sulfonamides which can be used to lower and control IOP. The compounds are formulated in pharmaceutical compositions for delivery.

The invention is also directed to methods for treating ocular hypertension and POAG by lowering and controlling IOP by the administration of the thiophene sulfonamides of the present invention. The compounds can be administered systemically and/or topically to the eye.

DETAILED DESCRIPTION OF THE INVENTION

The thiophene sulfonamides of the present invention have the following structure.

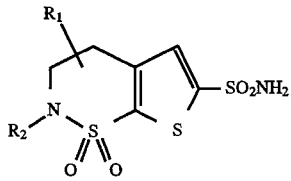

1 or a pharmaceutically acceptable salt thereof wherein:

$R_1$ is H; OH; $C_{1-6}$ alkoxy; $C_{1-6}$ alkyl unsubstituted or substituted optionally with OH, $NR_3R_4$, OC(=O)$R_5$ or C(=O)$R_5$; $NR_3R_4$; OC(=O)$R_5$; C(=O)$R_5$; $C_{2-4}$ alkoxy substituted optionally with OH, $NR_3R_4$, halogen, $C_{1-4}$ alkoxy or C(=O)$R_5$; phenyl or $R_6$ either of which can be unsubstituted or substituted optionally with OH, (CH$_2$)$_n$$NR_3R_4$, halogen, $C_{1-4}$ alkoxy, $C_{1-4}$ haloalkoxy, C(=O)$R_5$, S(=O)$_m$$R_7$ or SO$_2$$NR_3R_4$; wherein m is 0–2 and n is 0–2; provided that when $R_1$ is OH, alkoxy, $NR_3R_4$ or OC(=O)$R_5$ it is attached to the 4-position and when $R_1$ is $R_6$ and is attached to the 3 position, the $R_6$ ring is attached by a carbon carbon single bond.

$R_2$ is $C_{2-8}$ alkyl substituted with S(=O)$_m$$R_7$; $C_{4-7}$ alkenyl substituted with S(=O)$_m$$R_7$ wherein m is 0–2.

$R_3$ & $R_4$ are the same or different and are H; $C_{1-8}$ alkyl; $C_{2-4}$ alkyl substituted optionally with OH, halogen, $C_{1-4}$ alkoxy or C(=O)$R_5$; $C_{1-4}$ alkoxy; $C_{2-4}$ alkoxy substituted optionally with OH, halogen, $C_{1-4}$ alkoxy or C(=O)$R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, C(=O)$R_5$, $C_{1-6}$ alkyl, $C_{1-6}$ alkyl substituted optionally with OH, halogen, $C_{1-4}$ alkoxy, C(=O)$R_5$ or on nitrogen with $C_{1-4}$ alkoxy, C(=O)$R_5$, S(=O)$_m$$R_7$, $C_{1-6}$ alkyl or $C_{2-6}$ alkyl substituted optionally with OH, halogen, $C_{1-4}$ alkoxy, C(=O)$R_5$ or on sulfur by (=O)$_m$, wherein m is 0–2.

$R_5$ is $C_{1-8}$ alkyl; $C_{1-8}$ alkyl substituted optionally with OH, $NR_3R_4$, halogen, $C_{1-4}$ alkoxy or C(=O)$R_8$; $C_{1-4}$ alkoxy; $C_{2-4}$ alkoxy substituted optionally with OH, $NR_3R_4$, halogen or $C_{1-4}$ alkoxy; or $NR_3R_4$.

$R_6$ is a monocyclic ring system of 5 or 6 atoms composed of C, N, O and/or S, such as furan, thiophene, pyrrole, pyrazole, imidazole, triazole, tetrazole, oxazole, isoxazole, isothiazole, thiazole, thiadiazole, pyridine pyrimidine, pyridazine, and pyrazine.

$R_7$ is $C_{1-4}$ alkyl; $C_{3-5}$ alkenyl, $C_{2-4}$ alkyl substituted optionally with OH, $NR_3R_4$, $C_{1-4}$ alkoxy or C(=O)$R_5$; phenyl or $R_6$ either of which can be unsubstituted or substituted optionally with OH, (CH$_2$)$_n$$NR_3R_4$, halogen, $C_{1-4}$ alkoxy, $C_{1-4}$ haloalkoxy, C(=O)$R_5$, S(=O)$_m$$C_{1-4}$ alkyl or SO$_2$$NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

In the above definitions, the total number of carbon atoms in a substituent group is indicated by the $C_{i-j}$ prefix where i and j are numbers from 1 to 8, for example. This $C_{i-j}$ definition includes both the straight and branched chain isomers. For example, $C_{1-3}$ alkyl would designate methyl through the butyl isomers; and $C_{1-3}$ alkoxy would designate methoxy through the butoxy isomers.

The term "halogen" either alone or in compound words such as "haloalkyl," means fluorine, chlorine, bromine, or iodine. Further, when used in compound words such as "haloalkyl," said alkyl may be partially or fully substituted with halogen atoms, which may be the same or different.

Many of the novel compounds of the structure 1 possess one or more chiral centers and this invention includes all enantiomers, diastereomers, and mixtures thereof.

Compounds of the present invention can be prepared using the methods described below in Equations 1 to 3.

Compounds 1b, where the thioether group has been oxidized to the corresponding sulfone or sulfoxide, can be prepared directly from the corresponding thioether of 1a by the action of a mild oxidizing agent (Equation 1). Either the sulfoxide or sulfone can be prepared selectively by varying the reaction conditions, temperature, and stoichiometry based on known methods. Oxidizing agents useful for these conversions include mCPBA, Oxone®, hydrogen peroxide and other similar reagents.

Equation 1

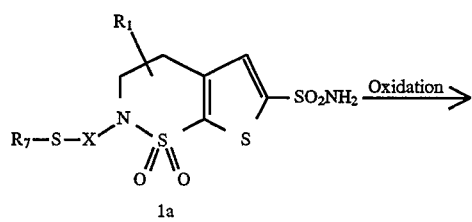

1a

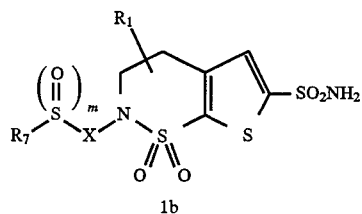

1b

Wherein $R_1$, $R_7$, and m are as previously defined and X is $C_{2-8}$ alkyl or $C_{4-7}$ alkenyl.

The most direct method useful for the preparation of the thioether compounds 1a in particular those wherein the $R_1$ group is an alkyl amine group, is shown in Equation 2. This method features the introduction of the key thioether moiety in the last step of the synthesis. In this method the basic ring structure is assembled initially and then converted into a suitable substrate for the introduction of the thioether group. This is accomplished by preparing compounds of structure 3 which possess a suitable leaving group attached to the appropriate X substituent. This key intermediate is converted directly to the compounds 1a via nucleophilic displacement of the leaving group with the appropriate thiolate anion. This transformation can be accomplished by adding the compounds 3 to the thiolate anion in a polar aprotic solvent such as N,N-dimethylformamide (DMF) or dimethylsulfoxide (DMSO) at temperatures ranging from 0° to 65°. After the reaction is judged to be complete, as analyzed by thin layer chromatography (TLC), high pressure liquid chromatography (HPLC), or gas chromatography (GC) (or other means known to one skilled in the art), the reaction mixture is added to water and the desired product is isolated either by filtration or by extraction (or other methods known to one skilled in the art). The desired compounds 1a can be isolated in pure form by recrystallization. The preparation of the desired thiolate anions is known. Compounds 3 can be prepared from compounds 4 according to Equation 3.

Equation 2

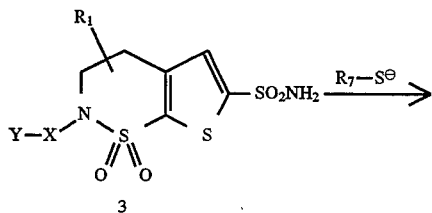

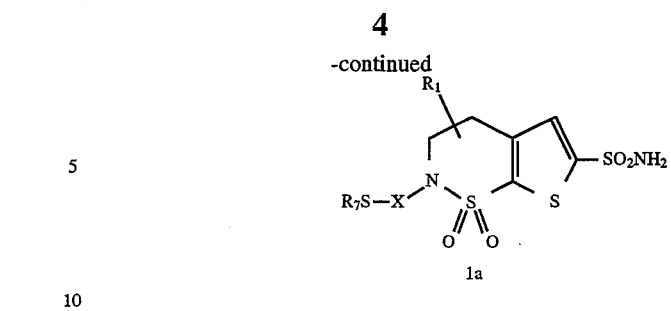

1a

Wherein: $R_1$ is $NR_5R_4$, and X and $R_7$ are as previously defined; and Y is a leaving group such as Cl, Br, I, $OSO_2CH_3$, $OSO_2(p\text{-}CH_3Ph)$ or similar leaving group.

Compounds 1 were the $R_1$ group is other than an amine group can be prepared from compounds of structure 4 (Equation 3). The cyclic sulfonamide group of compounds of structure 4 can be alkylated selectively using alkylating agents which already possess the key thioether moiety. The compounds 4 are then converted to the compounds 1 using standard deprotection conditions. The compounds 4 are known in the art.

Equation 3

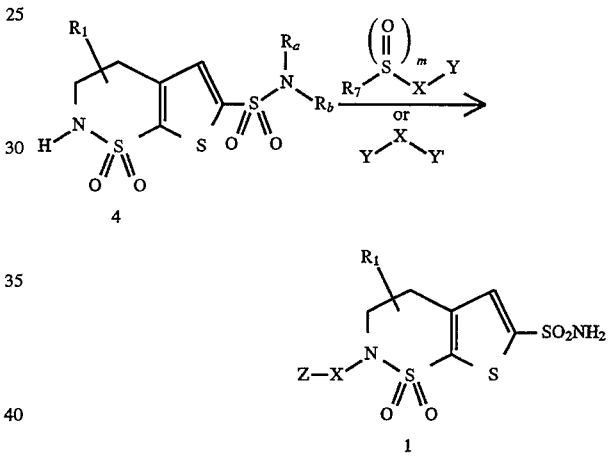

Wherein: $R_1$, $R_7$, X, m, and Y are as previously defined; Y' is Y; Z is $R_7\text{-}S(=O)_m$ and Y; $R_a$ and $R_b$ represent protecting groups for the sulfonamide such as H, t-butyl, a formamidine group, an imidate group and/or other similar functionalities.

The compounds of the present invention are exceptionally active relative to known compounds and some are believed to have much shorter half lifes. It is advantageous to have a short half life because the compounds have been designed to be effective upon topical application to the eye. Most of the compound that leaves the eye, for example, via the lacrimal punctum, is absorbed systemically. Compounds with shorter half lives are believed to cause fewer undesirable systemic side effects.

The compounds can be incorporated into various types of ophthalmic formulations for delivery to the eye. These compounds may be combined with ophthalmologically acceptable preservatives, surfactants, viscosity enhancers, penetration enhancers, buffers, sodium chloride, and water to form an aqueous, sterile ophthalmic suspension or solution. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, Carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. A thickener, such as hydroxymethylcellulose, hydroxypropylmethylcellulose, methylcellulose, polyvinylpyrrolidone, or the like, to improve the retention of the medicament in the conjunctival sac.

The compounds are preferably formulated as topical ophthalmic suspensions or solutions, with a pH of about 4.5 to 8.0. The compounds will normally be contained in these formulations in an amount of 0.1% to 10% by weight, but preferably in an amount of 0.25% to 5.0% by weight. Thus, for topical presentation these formulations would be delivered to the surface of a mammal's eye 1 to 3 times a day according to the routine discretion of a skilled clinician.

The following examples, which are in no way limiting, illustrate the preparation of selected examples of the compounds of the present invention. The compound set forth in Example 1 represents the preferred thiophene sulfonamide.

EXAMPLE 1

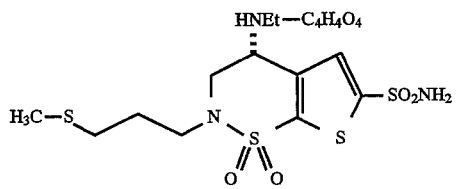

(+)-(R)-4-Ethylamino-3,4-dihydro-2-(3-methylthiopropyl)-2H-thieno-[3,2-e]-1,2-thiazine-6-sulfonamide 1,1-dioxide maleic acid Step A:

Preparation of 2-(3-Bromopropyl)-4-ethylamino-3,4-dihydro-2H-thieno-[3,2-e]-1,2-thiazine-6-sulfonamide 1,1-dioxide A stirred solution of (+)-(R)-4-ethylamino-3,4-dihydro-2-(3-methoxypropyl)-2H-thieno-[3,2-e]-1,2-thiazine-6-sulfonamide-1,1-dioxide hydrochloride (4.5 g, 110.7 mmol) in 48% HBr (20.0 mL) was heated at 80° C. for 72 h. The reaction mixture was concentrated in vacuo at 60° C. bath temperature to give a pale tan solid (4.8 g, 96%).

Step B:

Preparation of (+)-(R)-4-Ethylamino-3,4-dihydro-2-(3-methylthiopropyl)-2H-thieno-[3,2-e]-1,2-thiazine-6-sulfonamide 1,1-dioxide maleic acid To a stirred suspension of sodium thiomethoxide (1.18 g, 16.8 mmol) in DMF (5.0 mL) at room temperature was added a solution of the compound isolated in Step A above (1.48 g, 2.8 mmol) in DMF (10.0 mL). After 2 h, water (50.0 mL) was added and the mixture extracted with ethyl acetate (3×50.0 mL). Ethyl acetate extracts were combined, washed with brine (20.0 mL), dried (MgSO$_4$) and evaporated. The residue was purified by flash chromatography on silica (gradient: 50% ethyl acetate-hexane, 60% ethyl acetate-hexane, ethyl acetate) to yield a solid (1.16 g, 100%) which was dissolved in THF (5.0 mL) and added to a solution of maleic acid (0.44 g, 3.7 mmol) in ether. The volatiles were evaporated and the solid dried. Recrystallization from ethyl acetate gave the desired product (0.88 g): m.p. 151°–152° C.; [α]$_D$+8.36° (c=0.67; MeOH); Anal. Calcd for C$_{16}$H$_{25}$N$_3$O$_8$S$_4$; C, 37.27; H, 4.89, N, 8.15. Found C, 37.36; H, 4.93; N, 8.12.

Using modifications of the above procedure, but substituting the appropriate alkylamine in Step A the following compounds can be prepared:

1. 3,4-Dihydro-4-propylamino-2-(3-methylthiopropyl)-2H-thieno-[3,2-e]-1,2-thiazine-6-sulfonamide 1,1-dioxide hydrochloride;
2. 3,4-Dihydro-4-[(2-methylpropyl)amino]-2-(3-methylthiopropyl)-2H-thieno-[3,2-e]-1,2-thiazine-6-sulfonamide 1,1-dioxide hydrochloride;
3. 3,4-Dihydro-4-[(3-methylbutyl)amino]-2-(3-methylthiopropyl)-2H-thieno-[3,2-e]-1,2-thiazine-6-sulfonamide 1,1-dioxide hydrochloride;
4. 3,4-Dihydro-4-methylamino-2-(3-methylthiopropyl)-2H-thieno-[3,2-e]-1,2-thiazine-6-sulfonamide 1,1-dioxide hydrochloride.

EXAMPLE 2

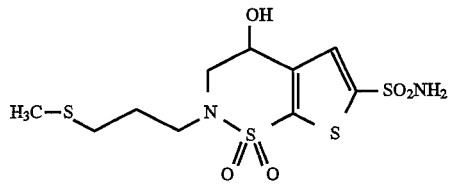

3,4-Dihydro-4-hydroxy-2-(3-methylthiopropyl)-2H-thieno-[3,2-e]-1,2-thiazine-6-sulfonamide 1,1-dioxide To a stirred solution of 3,4-dihydro-4-hydroxy-N-(1,1-dimethyl)ethyl-2H-thieno-[3,2-e]-1,2-thiazine-6-sulfonamide 1,1-dioxide (2.4 g, 7.1 mmol) in DMF (15.0 mL) was added NaH (60% dispersion in mineral oil, 0.508 g, 12.7 mmol) at 0° C. After 30 min, a solution of 3-methylthiopropane p-toluene sulfonate (3.3 g, 12.7 mmol) in DMF (3.0 mL) was added dropwise. The mixture was stirred an additional 5 h at which point TLC analysis indicated that the reaction was complete. The reaction mixture was poured into a saturated solution of ammonium chloride (20.0 mL) and the mixture extracted with ethyl acetate (4×50.0 mL). The ethyl acetate extracts were combined, washed with water and then brine (20.0 mL), dried (MgSO$_4$) and evaporated. The residue was purified by flash chromatography on silica (30% ethyl acetate-hexane, 40% ethyl acetate-hexane, 50% ethyl acetate-hexane) to yield the product as a yellow oil. Without further manipulation, TFA (20.0 mL) was added to the oil and the mixture stirred for 24 h after which time TLC analysis indicated that the reaction was finished. The TFA was evaporated and the residue was combined with saturated sodium bicarbonate solution and extracted with ethyl acetate (3×50 mL). The combined organic extracts were washed with brine (10 mL), dried (MgSO$_4$), and evaporated. The residue was purified by flash chromatography on silica (50% ethyl acetate-hexane) to furnish the desired product as an oil.

EXAMPLE 3

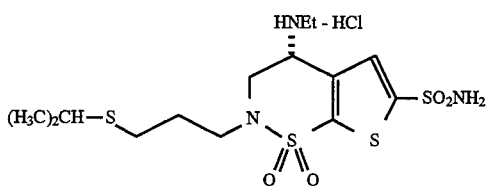

(R)-4-Ethylamino-3,4-dihydro-2-[3-(1-methylethylthio)propyl]-2H-thieno-[3,2-e]-1,2-thiazine-6-sulfonarnide 1,1-dioxide hydrochloride To a stirred suspension of sodium 2-propanethiolate (1.13 g, 11.6 mmol) in DMF (5.0 mL) at room temperature was added a solution of the compound prepared in Example 1, Step A, (0.99 g, 1.9 mmol) in DMF (10.0 mL). After 2 h, water (50.0 mL) was added and the mixture extracted with ethyl acetate (3×50.0 mL). Ethyl acetate extracts were combined, washed with brine (20.0 mL), dried (MgSO$_4$) and evaporated. The residue was purified by flash chromatography on silica (gradient: 50% ethyl acetate-hexane, 60% ethyl acetate-hexane, ethyl acetate) to yield a solid (0.78 g, 95%) which was dissolved in ethanol (5.0 mL) and added to a solution of ethanolic HCl (2 mL). The volatiles were evaporated and the solid dried. Recrystallization from methanol-methylene chloride gave the product (0.78 g): m.p. 165°–167° C.; [α]$_D$+6.88 (c=0.64; MeOH); Anal. Calcd for C$_{14}$H$_{26}$ClN$_3$O$_4$S$_4$·0.5 H$_2$O; C, 35.54; H, 5.75, N, 8.88. Found: C, 35.52; H, 5.71; N, 8.84.

Using modifications of the above procedure, but substituting the appropriate thiolate, the following compounds can be prepared:

1. 4-Ethylamino-3,4-dihydro-2-(3-propylthiopropyl)-2H-thieno-[3,2-e]-1,2-thiazine-6-sulfonamide 1,1-dioxide hydrochloride;
2. 4-Ethylamino-3,4-dihydro-2-(3-ethylthiopropyl)-2H-thieno-[3,2-e]-1,2-thiazine-6-sulfonamide 1,1-dioxide hydrochloride;
3. 4-Ethylamino-3,4-dihydro-2-[3-(2-methoxyethylthio)propyl]-2H-thieno-[3,2-e]-1,2-thiazine-6-sulfonamide 1,1-dioxide hydrochloride;
4. 4-Ethylamino-3,4-dihydro-2-[3-(3-methoxypropylthio)propyl]-2H-thieno-[3,2-e]-1,2-thiazine-6-sulfonamide 1,1-dioxide hydrochloride.

Using modifications of the above procedure and that described in Example 1, but substituting the appropriate thienothiazine in Step A, Example 1 and the desired thiolate, the following compounds can be prepared:

1. 4-Ethylamino-3,4-dihydro-2-[3-(2-methoxyethylthio)ethyl]-2H-thieno-[3,2-e]-1,2-thiazine-6-sulfonamide 1,1-dioxide hydrochloride;
2. 4-Ethylamino-3,4-dihydro-2-[(2-methylthio)ethyl]-2H-thieno-[3,2-e]-1,2-thiazine-6-sulfonamide 1,1-dioxide hydrochloride;
3. 3,4-Dihydro-4-propylamino-2-[(2-methylthio)ethyl)]-2H-thieno-[3,2-e]-1,2-thiazine-6-sulfonamide 1,1-dioxide hydrochloride;
4. 3,4-Dihydro-4-[(2-methylpropyl)amino]-2-[(2-methylthio)ethyl]-2H-thieno-[3,2-e]-1,2-thiazine-6-sulfonamide 1,1-dioxide hydrochloride;
5. 4-Ethylamino-3,4-dihydro-2-[(4-methylthio)butyl]-2H-thieno-[3,2-e]-1,2-thiazine-6-sulfonamide 1,1-dioxide hydrochloride;
6. 3,4-Dihydro-4-propylamino-2-[(4-methylthio)butyl]-2H-thieno-[3,2-e]-1,2-thiazine-6-sulfonamide 1,1-dioxide hydrochloride;
7. 3,4-Dihydro-4-[(2-methylpropyl)amino]-2-[(4-methylthio)butyl]-2H-thieno-[3,2-e]-1,2-thiazine-6-sulfonamide 1,1-dioxide hydrochloride.

Using the procedures described in equations 1 to 3, Examples 1 to 3, and known procedures, one skilled in the art can prepare the compounds disclosed herein.

EXAMPLE 4

Ophthalmic Solution

| Ingredient | Concentration (wt %) |
| --- | --- |
| 3,4-Dihydro-4-ethylamino-2-(3-methylthiopropyl)-2H-thieno[3,2-e]-1,2-thiazine-6-sulfonamide-1,1-dioxide, Maleate (Compound) | 2.0% |
| Hydroxypropyl Methylcellulose | 3.0% |
| Sodium Acetate (Trihydrate) | 0.1% |
| Benzalkonium Chloride | 0.01% |
| Mannitol | 2.4% |
| Purified Water | q.s. |
| HCl/NaOH | pH 5.0 |

EXAMPLE 5

Ophthalmic Suspension

| Ingredient | Concentration (wt %) |
| --- | --- |
| 3,4-Dihydro-4-ethylamino-2-(3-methylthiopropyl)-2H-thieno[3,2-e]-1,2-thiazine-6-sulfonamide-1,1-dioxide (Compound) | 2.0% |
| Hydroxypropyl Methylcellulose | 3.0% |
| Dibasic Sodium Phosphate | 0.2% |
| Benzalkonium Chloride | 0.01% |
| Disodium Edetate | 0.01% |
| Polysorbate 80 | 0.05% |
| NaCl | 0.27% |
| Purified Water | q.s. |
| HCl/NaOH | pH 7.2 |

We claim:

1. A compound having the following structure:

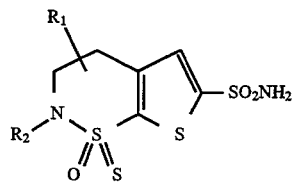

or a pharmaceutically acceptable salt thereof wherein:

R$_1$ is H; OH; C$_{1-6}$ alkoxy; C$_{1-6}$ alkyl unsubstituted or substituted optionally with OH, NR$_3$R$_4$, OC(=O)R$_5$ or C(=O)R$_5$; NR$_3$R$_4$; OC(=O)R$_5$; C(=O)R$_5$; C$_{2-4}$ alkoxy substituted optionally with OH, NR$_3$R$_4$, halogen, C$_{1-4}$ alkoxy or C(=O)R$_5$; phenyl or R$_6$ either of which can be unsubstituted or substituted optionally with OH, (CH$_2$)$_n$NR$_3$R$_4$, halogen, C$_{1-4}$ alkoxy, C$_{1-4}$ haloalkoxy, C(=O)R$_5$, S(=O)$_m$R$_7$ or SO$_2$NR$_3$R$_4$; wherein m is 0–2 and n is 0–2; provided that when R$_1$ is OH, alkoxy, NR$_3$R$_4$ or OC(=O)R$_5$ it is attached to the 4-position and when R$_1$ is R$_6$ and is attached to the 3 position, the R$_6$ ring is attached by a carbon carbon single bond;

$R_2$ is $C_{2-8}$ alkyl substituted with $S(=O)_mR_7$; $C_{4-7}$ alkenyl substituted with $S(=O)_mR_7$ wherein m is 0–2;

$R_3$ & $R_4$ are the same or different and are H; $C_{1-8}$ alkyl; $C_{2-4}$alkyl substituted optionally with OH, halogen, $C_{1-4}$ alkoxy or $C(=O)R_5$; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2;

$R_5$ is $C_{1-8}$ alkyl; $C_{1-8}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$;

$R_6$ is a monocyclic ring system selected from the group consisting of furan, thiophene, pyrrole, pyrazole, imidazole, triazole, tetrazole, oxazole, isoxazole, isothiazole, thiazole, thiadiazole, pyridine, pyrimidine, pyridazine, and pyrazine;

$R_7$ is $C_{1-4}$ alkyl; $C_{3-5}$ alkenyl, $C_{2-4}$ alkyl substituted optionally with OH, $NR_3R_4$, $C_{1-4}$ alkoxy or $C(=O)R_5$; phenyl or $R_6$ either of which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

2. The compound of claim 1 selected from the group consisting of:
(R)-4-Ethylamino-3,4-dihydro-2-(3-methylthiopropyl)-2H-thieno-[3,2-e]-1,2-thiazine-6-sulfonamide 1,1-dioxide;
3,4-Dihydro-4-propylamino-2-(3-methylthiopropyl)-2H-thieno-[3,2-e]-1,2-thiazine-6-sulfonamide 1,1-dioxide;
3,4-Dihydro-4-[(2-methylpropyl)amino]-2-(3-methylthiopropyl)-2H-thieno-[3,2-e]-1,2-thiazine-6-sulfonamide 1,1-dioxide;
3,4-Dihydro-4-[(3-methylbutyl)amino]-2-(3-methylthiopropyl)-2H-thieno-[3,2-e]-1,2-thiazine-6-sulfonamide 1,1-dioxide;
3,4-Dihydro-4-methylamino-2-(3-methylthiopropyl)-2H-thieno-[3,2-e]-1,2-thiazine-6-sulfonamide 1,1-dioxide;
3,4-Dihydro-4-hydroxy-2-(3-methylthiopropyl)-2H-thieno-[3,2-e]-1,2-thiazine-6-sulfonamide 1,1-dioxide;
(R)-4-Ethylamino-3,4-dihydro-2-[3-(1-methylethylthio)propyl]-2H-thieno-[3,2-e]-1,2-thiazine-6-sulfonamide 1,1-dioxide;
4-Ethylamino-3,4-dihydro-2-(3-propylthiopropyl)-2H-thieno-[3,2-e]-1,2-thiazine-6-sulfonamide 1,1-dioxide;
4-Ethylamino-3,4-dihydro-2-(3-ethylthiopropyl)-2H-thieno-[3,2-e]-1,2-thiazine-6-sulfonamide 1,1-dioxide;
4-Ethylamino-3,4-dihydro-2-[3-(2-methoxyethylthio)propyl]-2H-thieno-[3,2-e]-1,2-thiazine-6-sulfonamide 1,1-dioxide;
4-Ethylamino-3,4-dihydro-2-[3-(3-methoxypropylthio)propyl]-2H-thieno-[3,2-e]-1,2-thiazine-6-sulfonamide 1,1-dioxide;
4-Ethylamino-3,4-dihydro-2-[3-(2-methoxyethylthio)ethyl]-2H-thieno-[3,2-e]-1,2-thiazine-6-sulfonamide 1,1-dioxide;
4-Ethylamino-3,4-dihydro-2-[(2-methylthio)ethyl]-2H-thieno-[3,2-e]-1,2-thiazine-6-sulfonamide 1,1-dioxide;
3,4-Dihydro-4-propylamino-2-[(2-methylthio)ethyl)]-2H-thieno-[3,2-e]-1,2-thiazine-6-sulfonamide 1,1-dioxide;
3,4-Dihydro-4-[(2-methylpropyl)amino]-2-[(2-methylthio)ethyl]-2H-thieno-[3,2-e]-1,2-thiazine-6-sulfonamide 1,1-dioxide;
4-Ethylamino-3,4-dihydro-2-[(4-methylthio)butyl]-2H-thieno-[3,2-e]-1,2-thiazine-6-sulfonamide 1,1-dioxide;
3,4-Dihydro-4-propylamino-2-[(4-methylthio)butyl]-2H-thieno-[3,2-e]-1,2-thiazine-6-sulfonamide 1,1-dioxide; and
3,4-Dihydro-4-[(2-methylpropyl)amino]-2-[(4-methylthio)butyl]-2H-thieno-[3,2-e]-1,2-thiazine-6-sulfonamide 1,1-dioxide.

3. The compound of claim 2 which is (R)-4-Ethylamino-3,4-dihydro-2-(3-methylthiopropyl)-2H-thieno-[3,2-e]-1,2-thiazine-6-sulfonamide 1,1-dioxide.

4. A composition for lowering and controlling IOP comprising a pharmaceutically effective amount of a compound in an inert carrier, the compound having the following structure:

or a pharmaceutically acceptable salt thereof wherein:

$R_1$ is H; OH; $C_{1-6}$ alkoxy; $C_{1-6}$ alkyl unsubstituted or substituted optionally with OH, $NR_3R_4$, $OC(=O)R_5$ or $C(=O)R_5$; $NR_3R_4$; $OC(=O)R_5$; $C(=O)R_5$; $C_{2-4}$ alkoxy substituted optionally with OH, $NR_3R_4$, halogen, $C_{1-4}$ alkoxy or $C(=O)R_5$; phenyl or $R_6$ either of which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mR_7$ or $SO_2NR_3R_4$; wherein m is 0–2 and n is 0–2; provided that when $R_1$ is OH, alkoxy, $NR_3R_4$ or $OC(=O)R_5$ it is attached to the 4-position and when $R_1$ is $R_6$ and is attached to the 3 position, the $R_6$ ring is attached by a carbon carbon single bond;

$R_2$ is $C_{2-8}$ alkyl substituted with $S(=O)_mR_7$; $C_{4-7}$ alkenyl substituted with $S(=O)_mR_7$ wherein m is 0–2;

$R_3$ & $R_4$ are the same or different and are H; $C_{1-8}$ alkyl; $C_{2-4}$alkyl substituted optionally with OH, halogen, $C_{1-4}$ alkoxy or $C(=O)R_5$; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_m$, $R_7$, $C_{1-6}$ alkyl or $C_{2-6}$ alkyl substituted optionally with OH, halogen, $C_{1-4}$ alkoxy, $C(=O)R_5$ or on sulfur by $(=O)_m$, wherein m is 0–2;

$R_5$ is $C_{1-8}$ alkyl; $C_{1-8}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$;

$R_6$ is a monocyclic ring system selected from the group consisting of furan, thiophene, pyrrole, pyrazole, imidazole, triazole, tetrazole, oxazole, isoxazole, isothiazole, thiazole, thiadiazole, pyridine, pyrimidine, pyridazine, and pyrazine;

$R_7$ is $C_{1-4}$ alkyl; $C_{3-5}$ alkenyl, $C_{2-4}$ alkyl substituted optionally with OH, $NR_3R_4$, $C_{1-4}$ alkoxy or $C(=O)R_5$; phenyl or $R_6$ either of which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

5. The composition of claim 2 wherein the compound is selected from the group consisting of:
(R)-4-Ethylamino-3,4-dihydro-2-(3-methylthiopropyl)-2H-thieno-[3,2-e]-1,2-thiazine-6-sulfonamide 1,1-dioxide;
3,4-Dihydro-4-propylamino-2-(3-methylthiopropyl)-2H-thieno-[3,2-e]-1,2-thiazine-6-sulfonamide 1,1-dioxide;
3,4-Dihydro-4-[(2-methylpropyl)amino]-2-(3-methylthiopropyl)-2H-thieno-[3,2-e]-1,2-thiazine-6-sulfonamide 1,1-dioxide;
3,4-Dihydro-4-[(3-methylbutyl)amino]-2-(3-methylthiopropyl)-2H-thieno-[3,2-e]-1,2-thiazine-6-sulfonamide 1,1-dioxide;
3,4-Dihydro-4-methylamino-2-(3-methylthiopropyl)-2H-thieno-[3,2-e]-1,2-thiazine-6-sulfonamide 1,1-dioxide;
3,4-Dihydro-4-hydroxy-2-(3-methylthiopropyl)-2H-thieno-[3,2-e]-1,2-thiazine-6-sulfonamide 1,1-dioxide;
(R)-4-Ethylamino-3,4-dihydro-2-[3-(1-methylethylthio)propyl]-2H-thieno-[3,2-e]-1,2-thiazine-6-sulfonamide 1,1-dioxide;
4-Ethylamino-3,4-dihydro-2-(3-propylthiopropyl)-2H-thieno-[3,2-e]-1,2-thiazine-6-sulfonamide 1,1-dioxide;
4-Ethylamino-3,4-dihydro-2-(3-ethylthiopropyl)-2H-thieno-[3,2-e]-1,2-thiazine-6-sulfonamide 1,1-dioxide;
4-Ethylamino-3,4-dihydro-2-[3-(2-methoxyethylthio)propyl]-2H-thieno-[3,2-e]-1,2-thiazine-6-sulfonamide 1,1-dioxide;
4-Ethylamino-3,4-dihydro-2-[3-(3-methoxypropylthio)propyl]-2H-thieno-[3,2-e]-1,2-thiazine-6-sulfonamide 1,1-dioxide;
4-Ethylamino-3,4-dihydro-2-[3-(2-methoxyethylthio)ethyl]-2H-thieno-[3,2-e]-1,2-thiazine-6-sulfonamide 1,1-dioxide;
4-Ethylamino-3,4-dihydro-2-[(2-methylthio)ethyl]-2H-thieno-[3,2-e]-1,2-thiazine-6-sulfonamide 1,1-dioxide;
3,4-Dihydro-4-propylamino-2-[(2-methylthio)ethyl)]-2H-thieno-[3,2-e]-1,2-thiazine-6-sulfonamide 1,1-dioxide;
3,4-Dihydro-4-[(2-methylpropyl)amino]-2-[(2-methylthio)ethyl]-2H-thieno-[3,2-e]-1,2-thiazine-6-sulfonamide 1,1-dioxide;
4-Ethylamino-3,4-dihydro-2-[(4-methylthio)butyl]-2H-thieno-[3,2-e]-1,2-thiazine-6-sulfonamide 1,1-dioxide;
3,4-Dihydro-4-propylamino-2-[(4-methylthio)butyl]-2H-thieno-[3,2-e]-1,2-thiazine-6-sulfonamide 1,1-dioxide; and
3,4-Dihydro-4-[(2-methylpropyl)amino]-2-[(4-methylthio)butyl]-2H-thieno-[3,2-e]-1,2-thiazine-6-sulfonamide 1,1-dioxide.

6. The composition of claim 3 wherein the compound is (R)-4-Ethylamino-3,4-dihydro-2-(3-methylthiopropyl)-2H-thieno-[3,2-e]-1,2-thiazine-6-sulfonamide 1,1-dioxide.

7. A method for lowering and controlling IOP by administering to a human eye a pharmaceutically effective amount of a compound having the following structure:

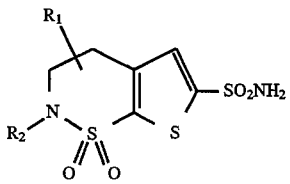

or a pharmaceutically acceptable salt thereof wherein:
$R_1$ is H; OH; $C_{1-6}$ alkoxy; $C_{1-6}$ alkyl unsubstituted or substituted optionally with OH, $NR_3R_4$, $OC(=O)R_5$ or $C(=O)R_5$; $NR_3R_4$; $OC(=O)R_5$; $C(=O)R_5$; $C_{2-4}$ alkoxy substituted optionally with OH, $NR_3R_4$, halogen, $C_{1-4}$ alkoxy or $C(=O)R_5$; phenyl or $R_6$ either of which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mR_7$ or $SO_2NR_3R_4$; wherein m is 0–2 and n is 0–2; provided that when $R_1$ is OH, alkoxy, $NR_3R_4$ or $OC(=O)R_5$ it is attached to the 4-position and when $R_1$ is $R_6$ and is attached to the 3 position, the $R_6$ ring is attached by a carbon carbon single bond;

$R_2$ is $C_{2-8}$ alkyl substituted with $S(=O)_mR_7$; $C_{4-7}$ alkenyl substituted with $S(=O)_mR_7$ wherein m is 0–2;

$R_3$ & $R_4$ are the same or different and are H; $C_{1-8}$ alkyl; $C_{2-4}$ alkyl substituted optionally with OH, halogen, $C_{1-4}$ alkoxy or $C(=O)R_5$; $C_{1-4}$ alkoxy; $C_{2-4}$ alkoxy substituted optionally with OH, halogen, $C_{1-4}$ alkoxy or $C(=O)R_5$; or $R_3$ and $R_4$ can be joined to form a ring of 5 or 6 atoms selected from O, S, C or N which can be unsubstituted or substituted optionally on carbon with OH, (=O), halogen, $C_{1-4}$ alkoxy, $C(=O)R_5$, $C_{1-6}$ alkyl, $C_{1-6}$ alkyl substituted optionally with OH, halogen, $C_{1-4}$ alkoxy, $C(=O)R_5$ or on nitrogen with $C_{1-4}$ alkoxy, $C(=O)R_5$, $S(=O)_mR_7$, $C_{1-6}$ alkyl or $C_{2-6}$ alkyl substituted optionally with OH, halogen, $C_{1-4}$ alkoxy, $C(=O)R_5$ or on sulfur by (=O)$_m$, wherein m is 0–2;

$R_5$ is $C_{1-8}$ alkyl; $C_{1-8}$ alkyl substituted optionally with OH, $NR_3R_4$, halogen, $C_{1-4}$ alkoxy or $C(=O)R_8$; $C_{1-4}$ alkoxy; $C_{2-4}$ alkoxy substituted optionally with OH, $NR_3R_4$, halogen or $C_{1-4}$ alkoxy; or $NR_3R_4$;

$R_6$ is a monocyclic ring system selected from the group consisting of furan, thiophene, pyrrole, pyrazole, imidazole, triazole, tetrazole, oxazole, isoxazole, isothiazole, thiazole, thiadiazole, pyridine, pyrimidine, pyridazine, and pyrazine;

$R_7$ is $C_{1-4}$ alkyl; $C_{3-5}$ alkenyl, $C_{2-4}$ alkyl substituted optionally with OH, $NR_3R_4$, $C_{1-4}$ alkoxy or $C(=O)R_5$; phenyl or $R_6$ either of which can be unsubstituted or substituted optionally with OH, $(CH_2)_nNR_3R_4$, halogen, $C_{1-4}$ alkoxy, $C_{1-4}$ haloalkoxy, $C(=O)R_5$, $S(=O)_mC_{1-4}$ alkyl or $SO_2NR_3R_4$; wherein m is 0–2 and n is 0–2; and $R_8$ is $C_{1-4}$ alkyl; $C_{1-4}$ alkoxy; amino, $C_{1-3}$ alkylamino, of di-$C_{1-3}$ alkylamino.

8. The method of claim 7 wherein the compound is selected from the group consisting of:
(R)-4-Ethylamino-3,4-dihydro-2-(3-methylthiopropyl)-2H-thieno-[3,2-e]-1,2-thiazine-6-sulfonamide 1,1-dioxide;
3,4-Dihydro-4-propylamino-2-(3-methylthiopropyl)-2H-thieno-[3,2-e]-1,2-thiazine-6-sulfonamide 1,1-dioxide;
3,4-Dihydro-4-[(2-methylpropyl)amino]-2-(3-methylthiopropyl)-2H-thieno-[3,2-e]-1,2-thiazine-6-sulfonamide 1,1-dioxide;
3,4-Dihydro-4-[(3-methylbutyl)amino]-2-(3-methylthiopropyl)-2H-thieno-[3,2-e]-1,2-thiazine-6-sulfonamide 1,1-dioxide;

3,4-Dihydro-4-methylamino-2-(3-methylthiopropyl)-2H-thieno-[3,2-e]-1,2-thiazine-6-sulfonamide 1,1-dioxide;

3,4-Dihydro-4-hydroxy-2-(3-methylthiopropyl)-2H-thieno-[3,2-e]-1,2-thiazine-6-sulfonamide 1,1-dioxide;

(R)-4-Ethylamino-3,4-dihydro-2-[3-(1-methylethylthio)propyl]-2H-thieno-[3,2-e]-1,2-thiazine-6-sulfonamide 1,1-dioxide;

4-Ethylamino-3,4-dihydro-2-(3-propylthiopropyl)-2H-thieno-[3,2-e]-1,2-thiazine-6-sulfonamide 1,1-dioxide;

4-Ethylamino-3,4-dihydro-2-(3-ethylthiopropyl)-2H-thieno-[3,2-e]-1,2-thiazine-6-sulfonamide 1,1-dioxide;

4-Ethylamino-3,4-dihydro-2-[3-(2-methoxyethylthio)propyl]-2H-thieno-[3,2-e]-1,2-thiazine-6-sulfonamide 1,1-dioxide;

4-Ethylamino-3,4-dihydro-2-[3-(3-methoxypropylthio)propyl]-2H-thieno-[3,2-e]-1,2-thiazine-6-sulfonamide 1,1-dioxide;

4-Ethylamino-3,4-dihydro-2-[3-(2-methoxyethylthio)ethyl]-2H-thieno-[3,2-e]-1,2-thiazine-6-sulfonamide 1,1-dioxide;

4-Ethylamino-3,4-dihydro-2-[(2-methylthio)ethyl]-2H-thieno-[3,2-e]-1,2-thiazine-6-sulfonamide 1,1-dioxide;

3,4-Dihydro-4-propylamino-2-[(2-methylthio)ethyl)]-2H-thieno-[3,2-e]-1,2-thiazine-6-sulfonamide 1,1-dioxide;

3,4-Dihydro-4-[(2-methylpropyl)amino]-2-[(2-methylthio)ethyl]-2H-thieno-[3,2-e]-1,2-thiazine-6-sulfonamide 1,1-dioxide;

4-Ethylamino-3,4-dihydro-2-[(4-methylthio)butyl]-2H-thieno-[3,2-e]-1,2-thiazine-6-sulfonamide 1,1-dioxide;

3,4-Dihydro-4-propylamino-2-[(4-methylthio)butyl]-2H-thieno-[3,2-e]-1,2-thiazine-6-sulfonamide 1,1-dioxide; and 3,4-Dihydro-4-[(2-methylpropyl)amino]-2-[(4-methylthio)butyl]-2H-thieno-[3,2-e]-1,2-thiazine-6-sulfonamide 1,1-dioxide.

9. The method of claim 8 wherein the compound is (R)-4-Ethylamino-3,4-dihydro-2-(3-methylthiopropyl)-2H-thieno-[3,2-e]-1,2-thiazine-6-sulfonamide 1,1-dioxide.

* * * * *